United States Patent [19]

Livingston et al.

[11] Patent Number: 4,898,994
[45] Date of Patent: Feb. 6, 1990

[54] PROCESS FOR MAKING 3,5-DIALKYL-4-HYDROXYBENZYL-SUBSTITUTED AROMATICS

[75] Inventors: Glen L. Livingston, Church Hill, Tenn.; John Borges; George L. Mina, both of Orangeburg, S.C.

[73] Assignee: Ethyl Corporation, Richmond, Va.

[21] Appl. No.: 257,981

[22] Filed: Oct. 14, 1988

[51] Int. Cl.$^4$ .................. C07C 37/11; C07C 39/12
[52] U.S. Cl. .................... 568/720; 568/731; 568/732
[58] Field of Search .................. 568/720, 731, 732

[56] References Cited

U.S. PATENT DOCUMENTS

| | | | |
|---|---|---|---|
| 3,845,142 | 10/1974 | Gurvich et al. | 568/720 |
| 3,925,488 | 12/1975 | Shin | 568/720 |
| 4,259,534 | 3/1981 | Gurvich et al. | 568/720 |

FOREIGN PATENT DOCUMENTS

| | | | |
|---|---|---|---|
| 2745879 | 4/1978 | Fed. Rep. of Germany | 568/720 |
| 0092237 | 7/1981 | Japan | 568/720 |

*Primary Examiner*—Werren B. Lone
*Attorney, Agent, or Firm*—Joseph D. Odenweller

[57] ABSTRACT

3,5-di-alkyl-4-hydroxybenzyl-substituted aromatics are made in improved yield by co-feeding 2,6-di-alkyl-4-alkoxymethyl phenol and sulfuric acid to a benzene compound, e.g. mesitylene, in an inert solvent at −10° to 50° C.

11 Claims, No Drawings

PROCESS FOR MAKING 3,5-DIALKYL-4-HYDROXYBENZYL-SUBSTITUTED AROMATICS

BACKGROUND

The compound 1,3,5-tri-methyl-2,4,6-tri-(3,5-di-tert-butyl-4-hydroxybenzyl) mesitylene is a commercial antioxidant (Ethanox ®330, product of Ethyl Corporation). This compound and a method of preparing it by reacting 3,5-di-tert-butyl-4-hydroxybenzyl alcohol and mesitylene together with sulfuric acid or a Friedel Crafts catalyst is described in Rocklin et al. U.S. Pat. No. 3,026,264.

Another method for making the above antioxidant is described in Gurvich et al. GB No. 1,327,542. According to Gurvich et al., 2,6-di-tert-butyl-4-methoxymethyl phenol and mesitylene acid are mixed in an inert solvent such as methylene chloride and stirred at 1°–5° C. while adding sulfuric acid.

The present invention is an improvement on the process described by Gurvich et al. which results in a substantial cost reduction.

SUMMARY OF THE INVENTION

According to the present invention, 3,5-dialkyl-4hydroxybenzyl-substituted aromatic compounds are prepared in increased yield and purity by co-feeding 2,6-dialkyl-4alkoxymethyl phenol and sulfuric acid to an aromatic compound such as durene or mesitylene. The new process not only improves yield but decreases the amount of 4,4'-alkylene bis (2,6-dialkylphenol) formed in the process. Such bisphenols are effective antioxidants in their own right but are undesirable in the 3,5-dialkyl-4-hydroxybenzyl-substituted aromatics made by the present invention.

DESCRIPTION OF THE PREFERRED EMBODIMENT

A preferred embodiment of the invention is a process for making a 3,5-dialkyl-4-hydroxybenzyl-substituted aromatic compound, said process comprising co-feeding (i) a 2,6-dialkyl-4-alkoxymethyl phenol and (ii) sulfuric acid to an aromatic compound selected from benzene or an alkyl-substituted benzene.

The 2,6-dialkyl-4-alkoxymethyl phenols include any such compound wherein the alkyl groups contain 1 to 20 or more carbon atoms. A few representative examples are: 2,6-di-methyl-4-methoxymethyl phenol; 2,6-di-ethyl-4-ethoxymethyl phenol; 2-methyl-6-ethyl-4-propoxymethyl phenol; 2,6-di-sec-butyl-4-methoxymethyl phenol; 2,6-di-isopropyl-4-methoxymethyl phenol; 2-methyl-6-tert-butyl-4-methoxymethyl phenol; 2-methyl-6-sec-dodecyl-4-butoxymethyl phenol; 2,6-di-sec-eicosyl-4-dodecyloxymethyl phenol; 2,6-di-tert-octyl-4-methoxymethyl phenol and the like.

In a more preferred embodiment, at least one of the 2,6-dialkyl groups is a tert-alkyl group. In a highly preferred embodiment the alkyl group in the alkoxymethyl group is a lower alkyl group containing 1–4 carbon atoms. In a still more preferred embodiment both alkyls in the dialkyl groups are tert-alkyls and the alkoxymethyl group is a methoxymethyl group. The most preferred phenol reactant is 2,6-di-tert-butyl-4-methoxymethyl phenol.

The aromatic compound can be any aromatic benzene compound having an unsubstituted nuclear position capable of substitution. These include benzene, naphthalene, phenol, p-cresol, durene, mesitylene and the like.

In a more preferred embodiment, the aromatic compound is an alkylbenzene compound such as toluene, xylene, durene, mesitylene, ethylbenzene and the like. The most preferred aromatic compound is mesitylene.

The reaction is preferably carried out in an inert solvent. Useful solvents include aliphatic and cycloaliphatic hydrocarbons and aliphatic halohyrocarbons. Examples are hexane, heptane, isooctane, cyclohexane, 1,2-dichloroethane, methylene chloride, methylene bromide, 1,1,2-trichloroethane and the like. The preferred solvents are the halohydrocarbons, especially methylene chloride.

The amount of solvent should be an amount that will serve to dissolve the aromatic compound and the 2,6-dialkyl-4-alkoxymethyl phenol at reaction temperature. A useful range when reacting 2,6-di-tert-butyl-4-methoxymethyl phenol with mesitylene using a methylene chloride solvent is about 150–500 parts by weight and more preferably 200–300 parts per 100 parts of mesitylene and 2,6-di-tert-butyl-4-methoxymethyl phenol. Part of the solvent may be charged to the reactor to dissolve mesitylene and part mixed with 2,6-di-tert-butyl-4-methoxymethyl phenol.

The ratio of 2,6-di-alkyl-4-alkoxymethyl phenol to aromatic compound should be at least one mole per equivalent of substituent positions in the aromatic compound. For example, one mole of durene has two equivalents of open nuclear positions and one mole of mesitylene has three equivalents of unsubstituted substituent positions.

In a preferred embodiment about 2.0–2.75 moles and more preferably 2.1–2.3 moles of 2,6-di-tert-butyl-4-methoxymethyl phenol would be used per mole of durene.

In another preferred embodiment about 3.0–4.0 moles and more preferably 3.25–3.75 moles of 2,6-di-tert-butyl-4-methoxymethyl phenol would be used per mole of mesitylene.

The sulfuric acid should be fairly concentrated. A useful concentration is about 70–100 weight percent $H_2SO_4$. In a more preferred embodiment about 75–98 weight percent $H_2SO_4$ is used. In a most preferred embodiment the sulfuric acid is about 80–90 weight percent $H_2SO_4$.

The amount of sulfuric acid should be an amount which causes the reaction to go substantially to completion. A useful range in which to experiment is about 1–100 percent based on the weight of the 2,6-dialkyl-4-alkoxymethyl phenol reactant. In a preferred embodiment the amount of $H_2SO_4$ in the sulfuric acid is about 0.5–0.8 parts by weight per part of 2,6-dialkyl-4-alkoxymethyl phenol.

The important feature of the invention is that at least a part of the 2,6-di-alkyl-4-alkoxymethyl phenol and sulfuric acid are simultaneously co-fed to the aromatic compound. In the prior art the 2,6-dialkyl-4-alkoxymethyl phenol and aromatic compound were mixed in the reactor together with a solvent and the sulfuric acid fed to this stirred mixture. In the present process the aromatic compound, e.g. mesitylene, and solvent, e.g. methylene chloride, are placed in the reactor. The 2,6-dialkyl-4-alkoxymethyl phenol which may optionally contain inert solvent and the sulfuric acid are concurrently fed to the reaction mixture over an extended period. The feed of each may be continuous or in increments during the course of the reaction. The rate of feed of each can vary but as a guide it is preferred that each feed rate is such that the feed of each is completed at about the same time.

In a preferred embodiment, it has been found that it is not necessary to co-feed all of the 2,6-dialkyl-4-alkoxyalkyl phenol ("phenolic") and sulfuric acid. Good results have been achieved by conducting the process in two stages. The first stage is conducted in a conventional manner except only part of the total phenolic and sulfuric acid are used. In the second stage called the "co-feed stage" the balance of the phenolic and sulfuric acid are concurrently co-fed.

In a more preferred embodiment about 30–60 weight percent of the total phenolic and sulfuric acid are used in the first stage and 40–70 weight percent of the total phenolic and sulfuric acid are co-fed in the second stage.

In a highly preferred embodiment, about one mole part of mesitylene, about 1–2.5 moles of 2,6-di-tert-butyl-4-methoxymethyl phenol and inert solvent are charged to said first stage and about 1–2.5 moles of 2,6-di-tert-butyl-4-methylmethoxy phenol is used in the second stage co-feed such that the total 2,6-di-tert-butyl-4-methylmethoxy phenol is about 3.25–4.0 moles.

In a still more preferred embodiment, about 0.5–1.0 parts by weight of 75–98 weight percent sulfuric acid is fed to said first stage at $-5°$ to $25°$ C. and about 0.1–1.0 parts by weight of 75–98 weight percent sulfuric acid is co-fed to said second co-feed stage at $-5°$ to $25°$ C.

The total reaction time will vary with the reaction scale. A useful time range is about 0.5–12 hours or longer.

The reaction will proceed at low temperatures. A useful reaction temperature range is about $-10°$ C. up to $50°$ C. More preferably the reaction is conducted at about $-5°$ C. up to $25°$ C.

The manner of carrying out the co-feed process is shown in the following example.

EXAMPLE

In a first stage, a reaction vessel was charged with 4.0 Kg of methylene chloride, 1.17 Kg (9.75 moles) of mesitylene and 13.65 Kg of 32.9 weight percent solution of 2,6-di-tert-butyl-4-methoxymethyl phenol (17.96 moles) in methylene chloride containing about 2.7 weight percent of other phenolic impurities. This solution was cooled to $5°$ C. and while stirring, 3.8 Kg of an 84 weight percent $H_2SO_4$ was slowly added. The mixture was then stirred for 30 minutes at $6°–7°$ C.

CO-FEED STAGE

Following the first stage an additional 4.0 Kg of methylene chloride was added. The two streams were co-fed to the stirred reaction mixture held at $5–7°$ C. One stream was 13.65 Kg of the 32.9 weight percent solution of 2,6-di-tert-butyl-4-methoxymethyl phenol (17.96 moles) in methylene chloride and the other was 4.4 Kg of 84 weight percent $H_2SO_4$. The first stream was fed at about 95 g/min (143.7 min.) and the $H_2SO_4$ stream at 25 g/min (176 min). The reaction mixture was stirred an additional 45 minutes and then allowed to settle. The spent acid layer was separated and the crude reaction mixture was analyzed to contain 24.7 weight percent 1,3,5-tri-methyl-2,4,6-tri -(3,5-di-tert-butyl-4-hydroxybenzyl) benzene and about 5.3 weight percent of various phenolic impurities. The product was recovered by concentration and crystallization.

We claim:
1. A two-stage process for making a 3,5-di-$C_{1-20}$alkyl-4-hydroxybenzyl-substituted alkylbenzene compound, said process comprising a first stage of forming a mixture of said alkylbenzene compound and a 2,6-di-$C_{1-20}$-alkyl-4-methoxymethylphenol in an inert solvent, the amount of said 2,6-di-$C_{1-20}$-alkyl-4-methoxymethylphenol being about 30–60 weight percent of the total 2,6-di-$C_{1-20}$-alkyl-4-methoxymethylphenol used in the process and feeding sulfuric acid to said mixture at a temperature of about $-10°$ to $25°$ C. to form a first stage reaction mixture and a second co-feed stage of co-feeding (i) the remaining 40–70 weight percent of the 2,6-di-$C_{1-20}$-alkyl-4-methoxymethylphenol and (ii) sulfuric acid to form a final reaction mixture and recovering said 3,5-di-$C_{1-20}$-alkyl-4-hydroxybenzyl-substituted alkylbenzene compound from said final reaction mixture.

2. A process of claim 1 wherein said alkylbenzene compound is mesitylene.

3. A process of claim 2 wherein said 2,6-di-$C_1$-$C_{20}$-alkyl-4-methoxymethyl phenol is 2,6-di-tert-butyl-4-methoxymethyl phenol.

4. A process of claim 3 carried out in an inert solvent.

5. A process of claim 4 wherein said solvent is methylene chloride.

6. A process of claim 4 wherein about one mole part of mesitylene, about 1–2.5 moles of 2,6-di-tert-butyl-4-methoxymethyl phenol and inert solvent are charged to said first stage and about 1–2.5 moles of 2,6-di-tert-butyl-4-methoxymethyl phenol is used in the second stage co-feed such that the total 2,6-di-tert-butyl-4-methoxy methyl phenol is about 3.25–4.0 moles.

7. A process of claim 6 wherein about 0.5–1.0 parts by weight of 75–98 weight percent sulfuric acid is fed to said first stage at $-5°$ to $25°$ C. and about 0.1–1.0 parts by weight of 75–98 weight percent sulfuric acid is co-fed to said second co-feed stage at $-5°$ to $25°$ C.

8. A process of claim 7 wherein said solvent is methylene chloride in a total amount of 2–3 parts by weight per total amount of mesitylene and 2,6-di-tert-butyl-4-methoxymethyl phenol.

9. A two-stage process for making 1,3,5-trimethyl-2,4,6-tri(3,5-di-tert-butyl-4-hydroxybenzyl)benzene, said process comprising:
(A) forming a first mixture of 1–2.5 mole parts of 2,6-di-tert-butyl-4-methoxymethylphenol, one mole part of mesitylene and a solvent amount of an aliphatic halohydrocarbon and feeding about 0.5–1.0 parts by weight of 75–98 weight percent sulfuric acid per part of said 2,6-tert-butyl-4-methoxymethylphenol to said first mixture at a temperature of $-5°$ to $25°$ C. and
(B) in a second stage co-feeding (1) 1–2.5 mole parts of 2,6-di-tert-butyl-4-methoxymethylphenol and (2) 0.1–1.0 parts by weight 75–98 weight percent sulfuric acid per part of said 2,6-di-tert-butyl-4-methoxymethylphenol to the second stage reaction mixture such that the total amount of 2,6-di-tert-butyl-4-methoxymethylphenol is about 3.25 to 4.0 moles at a temperature of $-5°$ to $25°$ C.

10. A process of claim 9 wherein said solvent is methylene chloride.

11. A process of claim 10 wherein said first mixture comprises about 1.8 mole parts of 2,6-di-tert-butyl-4-methoxymethylphenol and 1 mole part of mesitylene and said second stage co-feed comprises about 1.8 mole parts of 2,6-di-tert-butyl-4-methoxymethylphenol. b

* * * * *